(12) United States Patent
Wieters et al.

(10) Patent No.: US 9,839,346 B2
(45) Date of Patent: Dec. 12, 2017

(54) SURGICAL INSTRUMENT

(75) Inventors: Martin Wieters, Hamburg (DE); Uwe Schoeler, Hoisdorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 84 days.

(21) Appl. No.: 13/254,764

(22) PCT Filed: Mar. 2, 2010

(86) PCT No.: PCT/EP2010/001277
§ 371 (c)(1),
(2), (4) Date: Sep. 2, 2011

(87) PCT Pub. No.: WO2010/099927
PCT Pub. Date: Sep. 10, 2010

(65) Prior Publication Data
US 2012/0029287 A1 Feb. 2, 2012

(30) Foreign Application Priority Data

Mar. 6, 2009 (DE) .................. 10 2009 011 479

(51) Int. Cl.
*A61B 1/00* (2006.01)
*A61B 1/05* (2006.01)
(Continued)

(52) U.S. Cl.
CPC .............. *A61B 1/05* (2013.01); *A61B 1/0011* (2013.01); *A61B 1/00018* (2013.01);
(Continued)

(58) Field of Classification Search
CPC ... A61B 19/5212; H01L 27/146; H01L 24/42; H01L 24/26; H01B 17/303; H01B 17/305; H01B 17/306; H01B 17/308; H02G 3/616
(Continued)

(56) References Cited

U.S. PATENT DOCUMENTS 4,677,471 A * 6/1987 Takamura et al. .............. 348/76
4,721,355 A * 1/1988 Gould .............................. 385/76
(Continued)

FOREIGN PATENT DOCUMENTS

DE 10 2006 030 543 A1 1/2007
DE 10 2006 015 176 B3 7/2007
(Continued)

OTHER PUBLICATIONS

International Search Report dated Jun. 11, 2010.
Japanese Office Action dated Sep. 3, 2013 in Japanese Patent Application No. 2011-552359.

*Primary Examiner* — Timothy J Neal
*Assistant Examiner* — Aaron B Fairchild
(74) *Attorney, Agent, or Firm* — Scully, Scott, Murphy & Presser, P.C.

(57) ABSTRACT

A surgical instrument having: a wall; an electrically insulating substrate; an electrical connection, wherein at least a portion of the electrical connection is applied on an exterior surface of the electrically insulating substrate; an insulating layer applied on the portion of the electrical connection; and a hermetic connection layer applied to the insulating layer, wherein the hermetic connection layer is hermetically connected to the wall to separate a hermetic chamber from an outer area.

15 Claims, 7 Drawing Sheets

Figure 1:
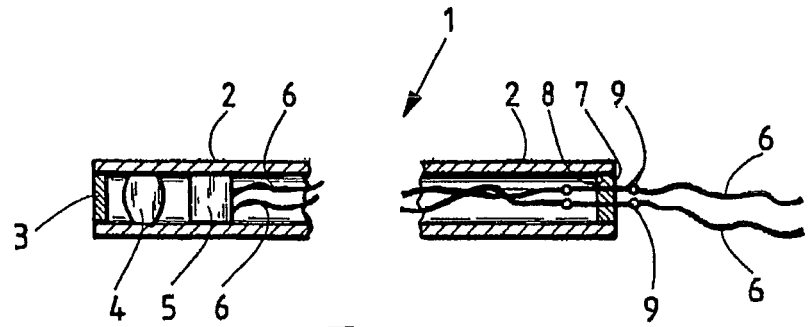

(51) Int. Cl.
| | |
|---|---|
| *H01B 17/26* | (2006.01) |
| *H01B 17/30* | (2006.01) |
| *H01L 23/00* | (2006.01) |
| *A61B 1/06* | (2006.01) |

(52) U.S. Cl.
CPC .......... *A61B 1/00114* (2013.01); *A61B 1/051* (2013.01); *H01B 17/26* (2013.01); *H01B 17/265* (2013.01); *H01B 17/303* (2013.01); *H01B 17/305* (2013.01); *H01L 24/26* (2013.01); *A61B 1/0676* (2013.01)

(58) Field of Classification Search
USPC .... 600/110, 109, 459, 101, 129, 132; 606/3; 439/579, 266, 626, 733.1; 174/255, 151, 174/152 R, 152 GM; 29/825, 854; 348/65, 76, 294
See application file for complete search history.

(56) References Cited

U.S. PATENT DOCUMENTS

| | | | | |
|---|---|---|---|---|
| 4,773,396 | A * | 9/1988 | Okazaki | 600/109 |
| 4,982,055 | A * | 1/1991 | Pollack et al. | 174/151 |
| 5,040,069 | A * | 8/1991 | Matsumoto et al. | 348/76 |
| 5,051,802 | A * | 9/1991 | Prost et al. | 257/434 |
| 5,231,248 | A | 7/1993 | Shah | |
| 5,729,437 | A * | 3/1998 | Hashimoto | 361/760 |
| 5,739,471 | A * | 4/1998 | Burisch | 174/102 R |
| 5,888,198 | A * | 3/1999 | Eggers et al. | 604/114 |
| 6,019,719 | A | 2/2000 | Schulz et al. | |
| 6,066,090 | A * | 5/2000 | Yoon | 600/113 |
| 6,080,101 | A | 6/2000 | Tatsuno et al. | |
| 6,390,972 | B1 * | 5/2002 | Speier et al. | 600/112 |
| 6,443,888 | B1 * | 9/2002 | Ogura et al. | 600/132 |
| 6,529,103 | B1 * | 3/2003 | Brendel et al. | 333/182 |
| 6,547,721 | B1 * | 4/2003 | Higuma et al. | 600/133 |
| 6,547,722 | B1 * | 4/2003 | Higuma et al. | 600/133 |
| 6,719,754 | B2 * | 4/2004 | Underwood et al. | 606/32 |
| 6,726,684 | B1 * | 4/2004 | Woloszko et al. | 606/32 |
| 7,094,967 | B2 * | 8/2006 | Evans et al. | 174/650 |
| 7,270,658 | B2 * | 9/2007 | Woloszko et al. | 606/32 |
| 7,399,273 | B2 * | 7/2008 | Moriyama et al. | 600/133 |
| 7,410,462 | B2 | 8/2008 | Navok et al. | |
| 7,429,260 | B2 * | 9/2008 | Underwood et al. | 606/32 |
| 7,449,021 | B2 * | 11/2008 | Underwood et al. | 606/32 |
| 7,462,178 | B2 * | 12/2008 | Woloszko et al. | 606/32 |
| 7,491,167 | B2 * | 2/2009 | Ogino et al. | 600/109 |
| 7,507,236 | B2 * | 3/2009 | Eggers et al. | 606/32 |
| 7,572,251 | B1 * | 8/2009 | Davison et al. | 604/500 |
| 7,628,752 | B2 * | 12/2009 | Yamamoto et al. | 600/109 |
| 7,641,610 | B2 * | 1/2010 | Nakamura et al. | 600/132 |
| 7,726,017 | B2 * | 6/2010 | Evans et al. | 29/854 |
| 7,819,863 | B2 * | 10/2010 | Eggers et al. | 606/32 |
| 7,892,164 | B2 * | 2/2011 | Segawa et al. | 600/109 |
| 7,940,296 | B2 * | 5/2011 | Ogino et al. | 348/65 |
| 8,095,224 | B2 * | 1/2012 | Truex et al. | 607/116 |
| 8,160,705 | B2 * | 4/2012 | Stevenson et al. | 607/32 |
| 8,360,967 | B2 * | 1/2013 | Yamamoto | 600/176 |
| 2002/0027484 | A1 * | 3/2002 | Stevenson et al. | 333/182 |
| 2002/0040180 | A1 * | 4/2002 | Hirano | 600/132 |
| 2002/0138082 | A1 * | 9/2002 | Brock et al. | 606/130 |
| 2002/0151885 | A1 * | 10/2002 | Underwood et al. | 606/41 |
| 2003/0028189 | A1 * | 2/2003 | Woloszko et al. | 606/45 |
| 2003/0040742 | A1 * | 2/2003 | Underwood et al. | 606/32 |
| 2003/0088245 | A1 * | 5/2003 | Woloszko et al. | 606/41 |
| 2003/0097126 | A1 * | 5/2003 | Woloszko et al. | 606/41 |
| 2003/0097129 | A1 * | 5/2003 | Davison et al. | 606/41 |
| 2003/0169333 | A1 | 9/2003 | Yazawa et al. | |
| 2003/0213604 | A1 * | 11/2003 | Stevenson et al. | 174/35 R |
| 2003/0234363 | A1 * | 12/2003 | Sekine et al. | 250/370.11 |
| 2004/0024398 | A1 * | 2/2004 | Hovda et al. | 606/41 |
| 2004/0024399 | A1 * | 2/2004 | Sharps et al. | 606/41 |
| 2004/0049180 | A1 * | 3/2004 | Sharps et al. | 606/41 |
| 2004/0082859 | A1 * | 4/2004 | Schaer | 600/459 |
| 2004/0153057 | A1 * | 8/2004 | Davison | 606/41 |
| 2005/0007718 | A1 * | 1/2005 | Stevenson et al. | 361/118 |
| 2005/0061530 | A1 * | 3/2005 | Evans et al. | 174/65 G |
| 2005/0065402 | A1 * | 3/2005 | Moriyama et al. | 600/133 |
| 2005/0171529 | A1 * | 8/2005 | Eggers et al. | 606/41 |
| 2005/0187543 | A1 * | 8/2005 | Underwood et al. | 606/32 |
| 2005/0190527 | A1 * | 9/2005 | Stevenson et al. | 361/302 |
| 2005/0248907 | A1 * | 11/2005 | Stevenson et al. | 361/306.2 |
| 2005/0288665 | A1 * | 12/2005 | Woloszko | 606/41 |
| 2006/0221543 | A1 * | 10/2006 | Stevenson et al. | 361/302 |
| 2006/0278431 | A1 * | 12/2006 | Evans et al. | 174/650 |
| 2007/0004964 | A1 * | 1/2007 | Ogino et al. | 600/109 |
| 2007/0004965 | A1 * | 1/2007 | Ogino et al. | 600/110 |
| 2007/0007360 | A1 * | 1/2007 | Ogino et al. | 235/495 |
| 2007/0008407 | A1 * | 1/2007 | Yamamoto et al. | 348/65 |
| 2007/0010706 | A1 * | 1/2007 | Yamamoto et al. | 600/109 |
| 2007/0035910 | A1 * | 2/2007 | Stevenson | 361/302 |
| 2007/0038024 | A1 * | 2/2007 | Nakamura et al. | 600/110 |
| 2007/0112346 | A1 * | 5/2007 | Underwood et al. | 606/41 |
| 2007/0219435 | A1 * | 9/2007 | Segawa et al. | 600/302 |
| 2008/0004615 | A1 * | 1/2008 | Woloszko et al. | 606/32 |
| 2008/0004621 | A1 * | 1/2008 | Dahla et al. | 606/48 |
| 2008/0009847 | A1 * | 1/2008 | Ricart et al. | 606/32 |
| 2008/0021447 | A1 * | 1/2008 | Davison et al. | 606/41 |
| 2008/0080051 | A1 * | 4/2008 | Yamamoto | 359/513 |
| 2008/0086033 | A1 | 4/2008 | Mihalca | |
| 2008/0243117 | A1 * | 10/2008 | Sharps et al. | 606/41 |
| 2008/0319506 | A1 * | 12/2008 | Cauller | 607/46 |
| 2009/0051763 | A1 * | 2/2009 | Adler et al. | 348/65 |
| 2009/0054786 | A1 * | 2/2009 | Beckermus | 600/476 |
| 2009/0054787 | A1 * | 2/2009 | Adler et al. | 600/476 |
| 2009/0069807 | A1 * | 3/2009 | Eggers et al. | 606/48 |
| 2009/0118618 | A1 * | 5/2009 | Harhen | 600/459 |
| 2009/0149852 | A1 * | 6/2009 | Eggers et al. | 606/45 |

FOREIGN PATENT DOCUMENTS

| | | | |
|---|---|---|---|
| DE | 196 47 855 B4 | 9/2007 | |
| EP | 0 594 793 B1 | 9/1995 | |
| EP | 1 455 216 A1 | 9/2004 | |
| JP | 06-250103 A | 9/1994 | |
| JP | 10-172628 A | 6/1998 | |
| JP | 10172628 A * | 6/1998 | ............ H01R 9/03 |
| JP | 10-262927 A | 10/1998 | |
| JP | 2001-037713 A | 2/2001 | |
| JP | 2002-124334 A | 4/2002 | |
| JP | 2003-190085 A | 7/2003 | |
| JP | 2004-261362 | 9/2004 | |
| JP | 2004-261362 A | 9/2004 | |
| JP | 2007-007228 A | 1/2007 | |
| JP | 2008-131200 A | 6/2008 | |
| JP | 2008-245668 A | 10/2008 | |

* cited by examiner

SURGICAL INSTRUMENT

CROSS-REFERENCE TO RELATED APPLICATIONS

This application claims priority to PCT Application EP2010/001277 filed on Mar. 2, 2010, which claims priority to Application No. DE 10 2009 011 479.3 filed on Mar. 6, 2009, the contents of each of which are incorporated herein by reference.

DISCRIPTION

The invention relates to a surgical instrument having a hermetic chamber, wherein at least one electrical connection from the hermetic chamber to outside the hermetic chamber to an outer area is provided.

This type of surgical instrument is known for example from DE 10 2006 015 176 B3 and is also shown for example in FIG. 1 of this patent application.

A rigid medical video endoscope with a system tube is shown there, which is provided distally with a window and which receives an objective and a video camera in its distal end area, which is connected to the outside with electrical lines through a proximal opening of the system tube, wherein the lines in the opening pass through a sealing made of potting material.

The object of the invention is to offer an alternative solution for providing a surgical instrument with a hermetic chamber, wherein in particular the electrical conductor lead-through should be designed hermetically.

This object is solved through a surgical instrument with a hermetic chamber, wherein at least one electrical connection from the hermetic chamber to outside the hermetic chamber to an outer area is provided, wherein the at least one electrical connection is applied to an electrically insulating substrate, wherein a first insulating layer is applied at least to the electrical connection and a layer suitable for a hermetic connection is applied to the first insulating layer, which is hermetically connected with a wall of the surgical instrument.

The electrical connection can hereby be for example a conductor path or a cable or a lead. The hermetic chamber in the surgical instrument is thus produced at least through a multi-layer applied to the electrically insulating substrate in connection with a wall, which is hermetically connected for example with an outer tube of the surgical instrument. A feed-through device comprising a substrate, at least one electrical connection and an insulating layer and at least one metal layer is thus formed. These layers are hereby permanently connected with each other, in particular via chemical connections or chemical bonds. The metal layer then serves as the layer suitable for the hermetic connection. The electrical connection is also permanently connected with the substrate and the insulating layer, in particular via chemical connections or chemical bonds.

The surgical instrument thus has a feed-through device, which is hermetically connected in a tube of the surgical instrument with the tube.

The other side of the hermetic chamber of the surgical instrument can for example be in the area of a window as in DE 10 2006 015 176 B3, where a hermetic sealing is provided. This can also be in the area of a crystal filter as in DE 196 47 855 B4. The hermetic connection described in this invention thus preferably concerns the proximal area of the surgical instrument. It could however also be used on the distal end of the surgical instrument.

The hermetic connection is preferably a soldering. The electrical connection, which is applied to the electrically insulating substrate, can be an electrically conductive coating, for example a metal. The different layers or respectively also the electrical connection, which are applied accordingly as per the invention, can be applied by means of CVD (Chemical Vapor Deposition), electron sputtering, ion sputtering, laser ablation or similar methods. The layer suitable for the hermetic connection is preferably made of a metal, in particular gold or silver.

The hermetic chamber is preferably provided in a tube, in particular an endoscope, in particular a laparoscope. The tube can be cylindrical or also have a different shape.

Through the invention, tubes with very small diameters can be used since the hermetic feed-through of electrical lines or respectively electrical connections can be designed very small. Large-scale hermetic plug contacts, as shown in U.S. Pat. No. 7,410,462 B2 or in DE 196 47 855 B4, can be foregone.

The electrically insulating substrate preferably has a thermal conductivity of more than 1 W/mK, in particular more than 10 W/mK, in particular greater than 200 W/mK. A correspondingly high thermal conductivity is preferably provided in order to thus enable heat dissipation, for example of the heat, which is generated by lamps in the hermetic chamber. Suitable materials are for example a ceramic like boron nitride, which has a thermal conductivity of up to approx. 400 W/mK, aluminum nitride (180 W/mK to 200 W/mK), silicon carbide (60 W/mK to 160 W/mK), aluminum oxide (20 W/mK to 50 W/mK), silicon dioxide (1 W/mK to 10 W/mK), silicon nitride (approximately 30 W/mK to 180 W/mK).

The electrically insulating substrate is preferably at least a part of a flexible conductor plate, wherein in particular the at least one electrical connection is at least a conductor of a conductor plate.

Through this preferred embodiment, further connections of conductors, cables or flexible conductor plates to the electrical devices in the hermetic chamber are to be avoided since they themselves represent the electrical connection. The flexible conductor plate is then provided with the corresponding layers in order to thus enable a hermetic connection.

Several electrical connections are preferably provided, which are arranged in particular symmetrically around the substrate. Through this preferred measure, large amounts of data can be forwarded quickly and accordingly several devices requiring an electrical supply in the surgical instrument are provided with power.

A wall preferably extends from the tube in the area of the electrically insulating substrate, in particular radially inward, wherein the wall surrounds the electrically insulating substrate, in particular radially, and is connected circumferentially hermetically with the layer suitable for the hermetic connection.

Within the framework of the invention, radial means not necessarily just a circular extension inward. Tubes can also be provided, which are not circular in cross-section but are rather shaped differently, for example elliptically or quadratically or respectively rectangularly. Elliptical or polygonal tubes can also be provided. The electrically insulating substrate can also be designed angularly in cross-section, wherein the hermetic connection is also designed circumferentially hermetically, wherein in the framework of the invention the term radial refers to various geometric shapes.

The wall preferably comprises at least two shell elements, which are in particular joined together hermetically.

Furthermore, the object is solved through a surgical instrument with a hermetic chamber, wherein a majority of electrical connections from the hermetic chamber to outside the hermetic chamber to an outer area is provided, which preferably has the above characteristics according to the invention or respectively preferred and which is further characterized in that the plurality of electrical connections are applied to a surface of an electrically insulating body, wherein the body has a longitudinal extension from the hermetic chamber to outside the hermetic chamber, wherein the body is hermetically connected with a tube.

The tube is preferably a metal tube. By providing a majority of electrical connections on a surface of an electrically insulating body, it is possible in an easy manner to provide a plurality of electrical connections on a connection piece so that the electrical connection of electronic components for example in a video endoscope from a hermetically sealed area to outside the hermetically sealed area is enabled in a secure manner. In the case of video endoscopes, the number of electrical feed lines continues to grow with the development of the video cameras. For example, up to 39 connector pins are currently used. The construction of hermetically sealed plugs for example in a glass-potted connector or other hermetical seal increases in difficulty. The connector pins hereby become thinner and more sensitive.

Through the suggested surgical instrument or respectively the suggested feed-through device comprising the electrically insulating body with the majority of electrical connections, which are applied to a surface of the electrically insulating body, it is possible to use corresponding conductor paths instead of connector pins. The insulating body can be for example a ceramic pin with a longitudinal extension along which the electrical connections are also provided. Very small or respectively narrow electrical connections can hereby be provided. The electrically insulating body or respectively ceramic pin is preferably imprinted with the electric conductors or respectively electrical connections. The hereby created robust electrical connection can then for example be casted in a hermetically sealed manner with a glass-potted connector or other potting types.

Another layer is preferably applied at least to a part of the electrical connections, for example another ceramic layer or another insulating layer and a metallic layer to this layer, which is suitable for a hermetic connection. A hermetic connection to a tube, for example the outer tube of the surgical instrument, can then be performed on this metallic layer, for example through soldering on a surface extending from the outer tube of the surgical instrument inward.

The surface of the body is preferably imprinted with the majority of electrical connections and/or the electrical connections are applied in the form of a metallization to the surface of the body. The body preferably has grooves extending longitudinally axially, wherein at least a portion of the majority of the electrical connections is arranged in the grooves. A very large number of electrical feed lines or respectively connections can hereby be provided, which do not interfere with each other. Electrical connections can thus be provided in particular on at least two planes or respectively different layers.

In the case of a cylindrical insulating body, for example a corresponding ceramic pin, electrical connections are then preferably arranged on a diameter in the cut of the insulating body, which is for example smaller than the outer diameter of the insulating body. The electrical connections are hereby very well protected from damage. Moreover, almost double the number of electrical connections are preferably achieved in that further electrical connections are applied to another level, namely for example the outer surface on the outer diameter of the insulating body. The grooves preferably have a rectangular or V-shaped cross-section.

If preferably in the case of the V-shaped grooves in each case an electrical connection is applied to a flank of the respective groove, a relatively simple production of the electrical connection is possible. These can then be performed namely through imprinting or sputtering of a metal from one side during a rotation or several slow rotations of the electrical insulating body. The electrical connection can hereby completely fill a flank or also cover just one part. The electrical connection preferably ends at a distance from the outer surface of the insulating body in the respective groove. A portion of the majority of the electrical connections is preferably provided outside the grooves.

Within the framework of the invention, the term rectangular section of a groove also includes a U-shaped cross-section.

Furthermore, the tube is preferably the inner or outer tube of the surgical instrument or is hermetically sealed with the inner and outer tube of the surgical instrument. The inner and outer tube is thereby in particular a hermetically sealed tube.

Figure 2:
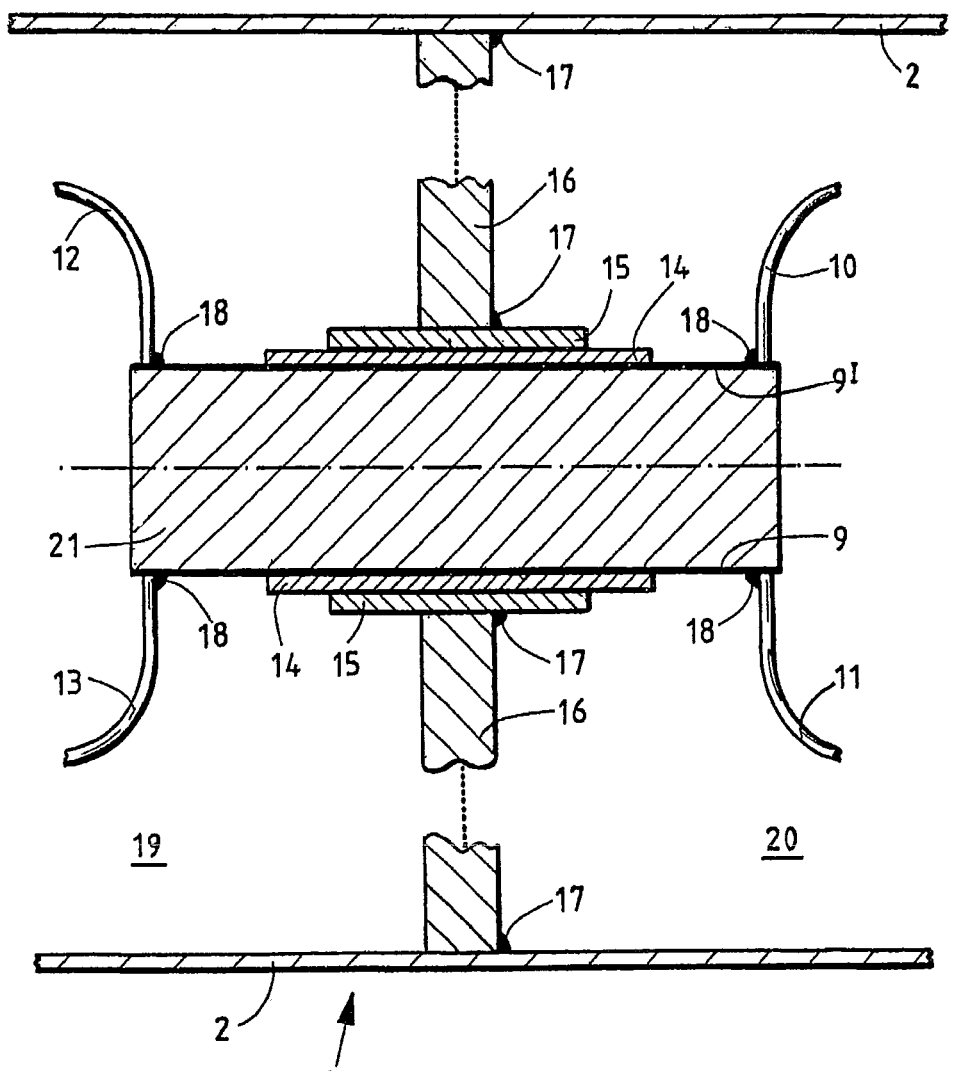
Figure 3:
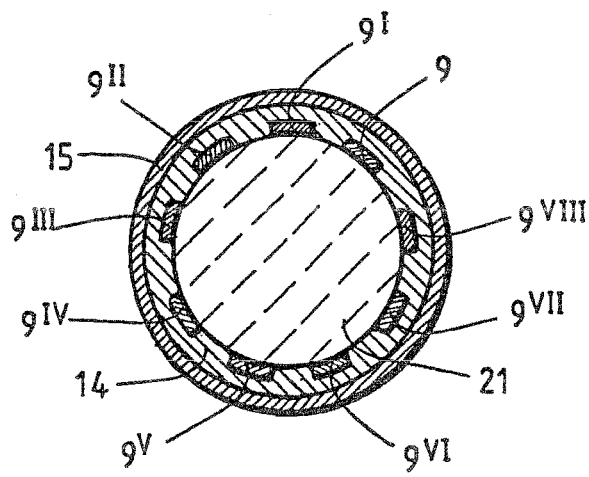
Figure 4:
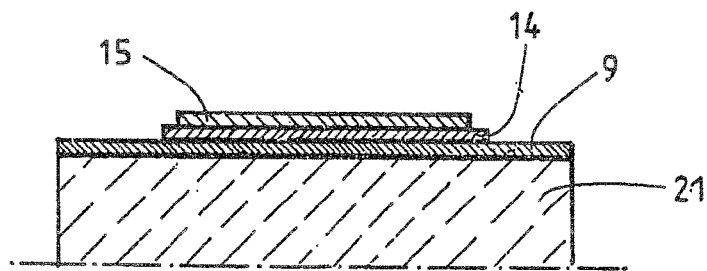
Figure 5:
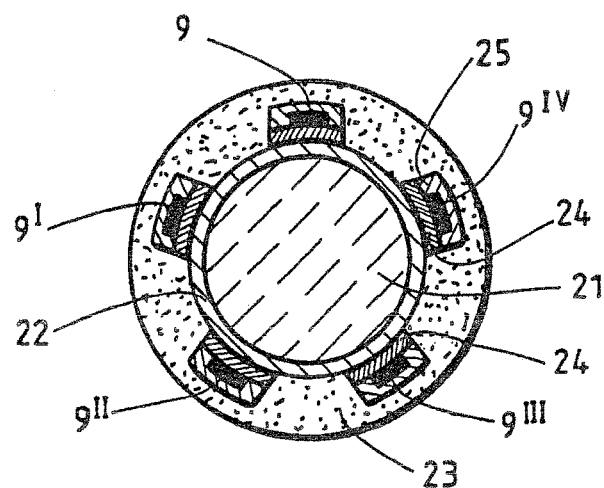
Figure 6:
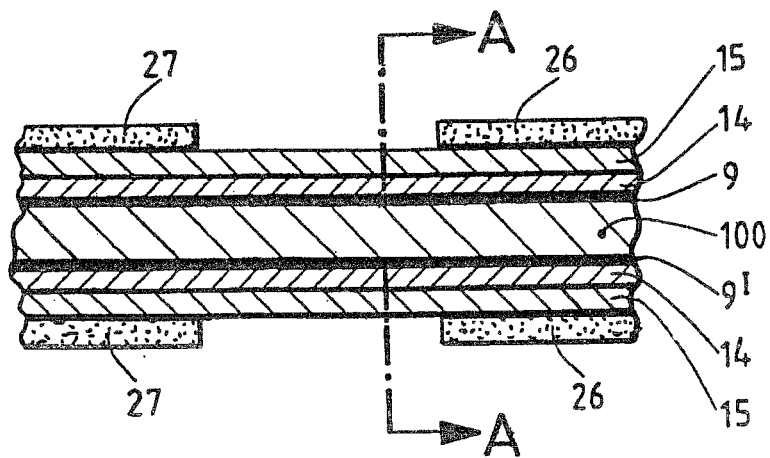
Figure 7:
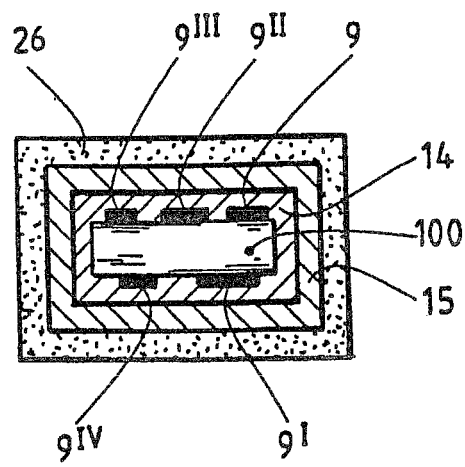
Figure 8:
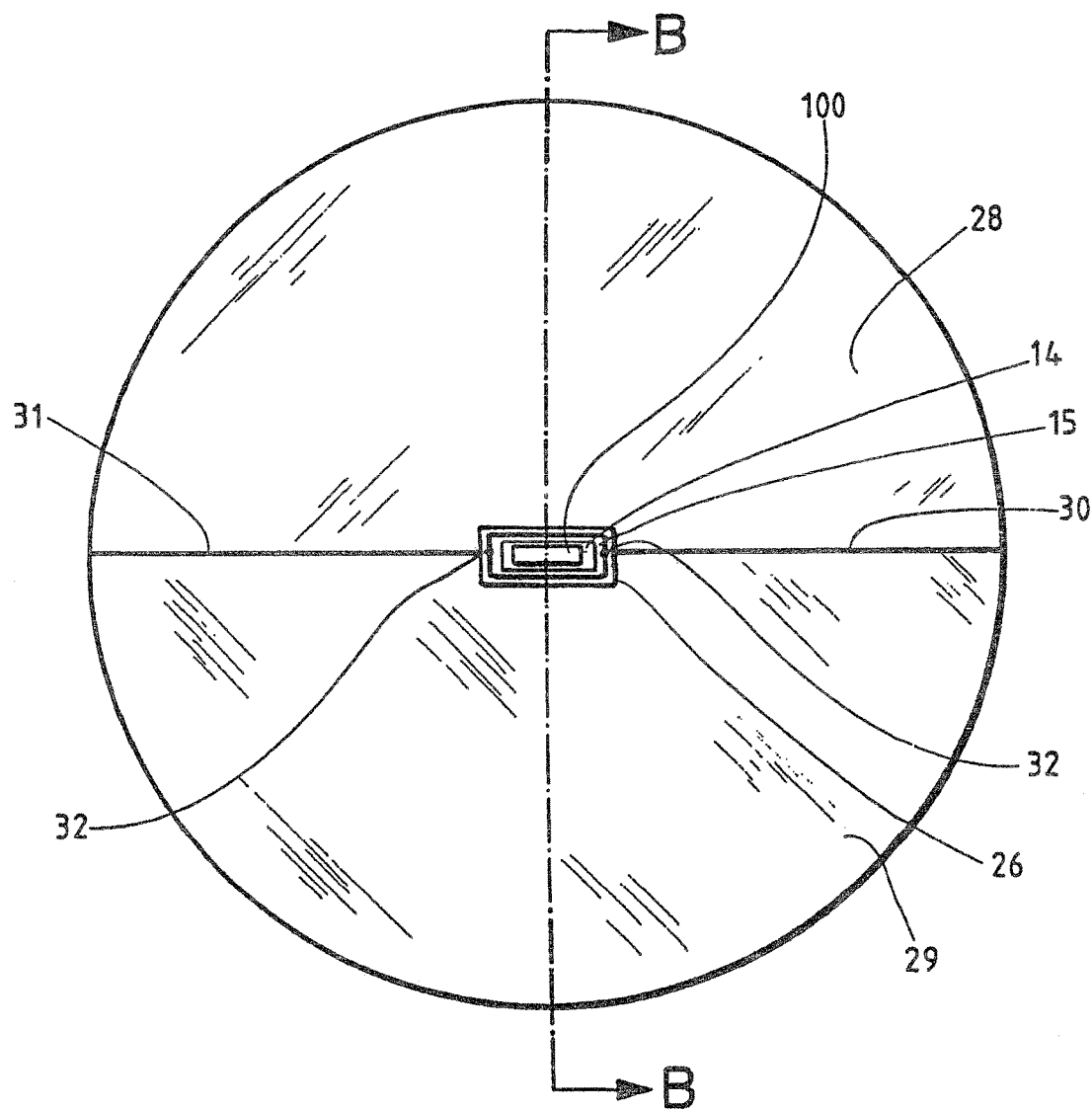
Figure 9:
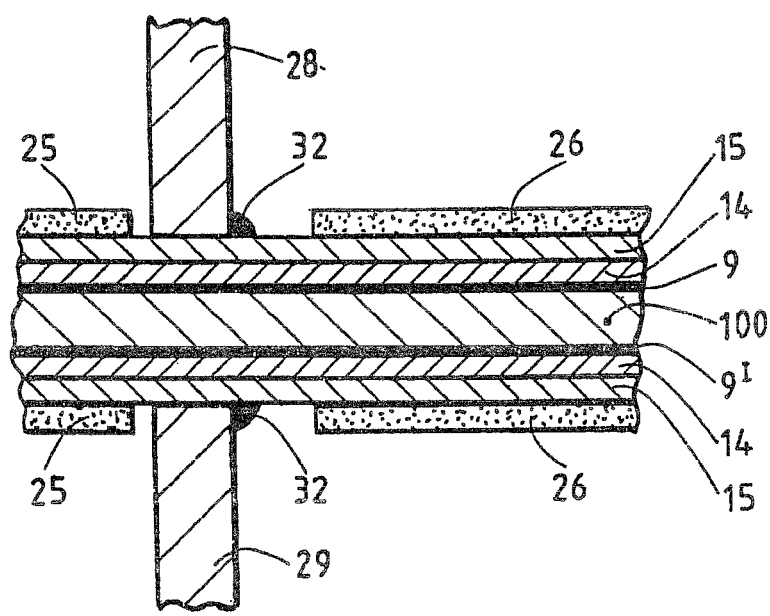
Figure 10:
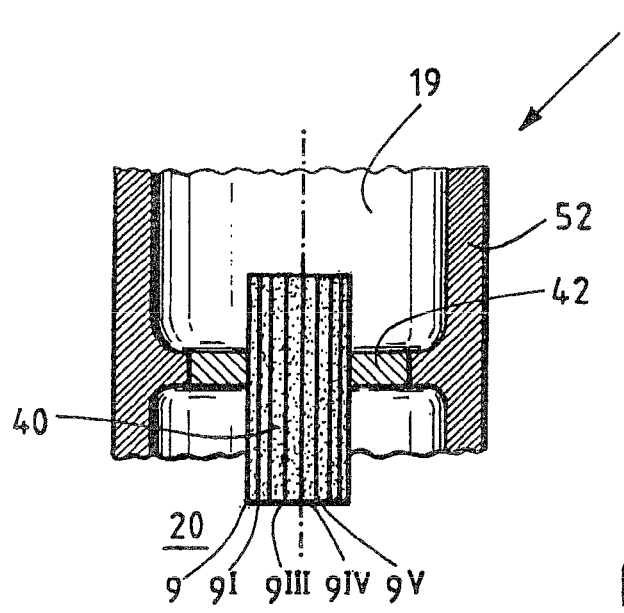
Figure 11:
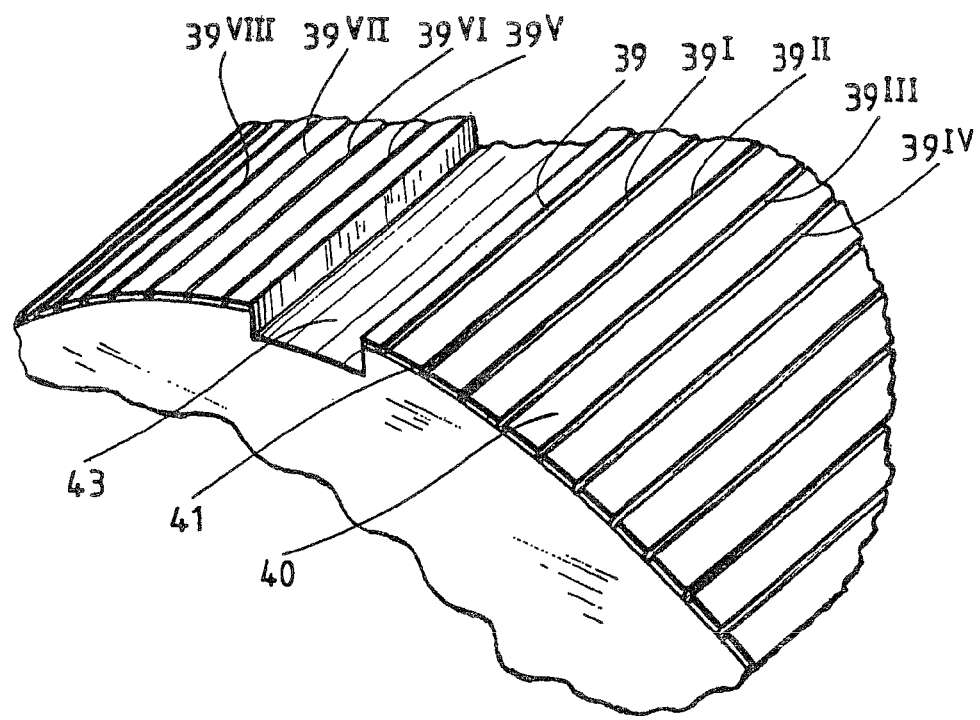
Figure 12:
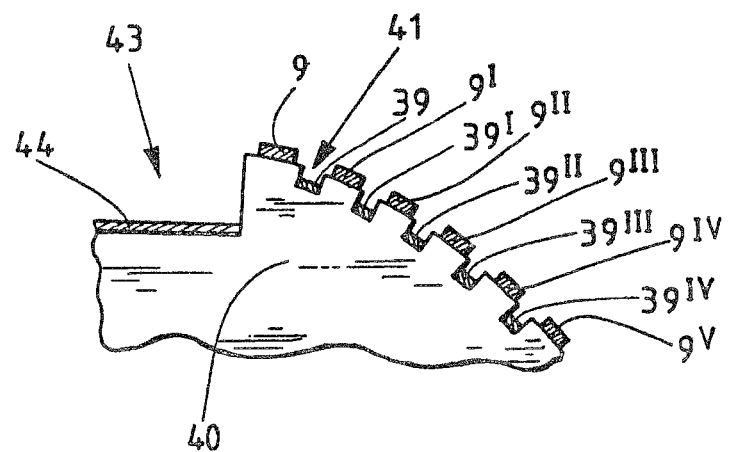
Figure 13:
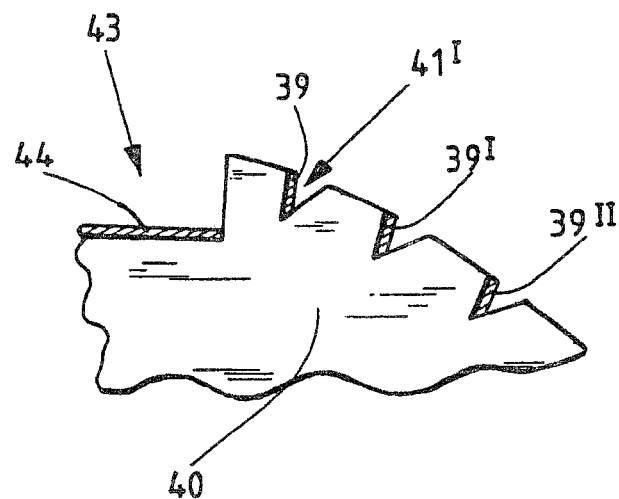

The invention is described below without restricting the general inventive idea based on exemplary embodiments with reference to the drawings, wherein the drawings are expressly referenced with respect to all details according to the invention not described in greater detail in the text. The drawings show in:

FIG. 1 a schematic longitudinal cut through a system tube of a video endoscope in accordance with the state of the art, FIG. 2 a schematic section of a longitudinal cut through a surgical instrument according to the invention, FIG. 3 a schematic radial sectional view of the embodiment in accordance with FIG. 2, FIG. 4 a schematic axial sectional view of a portion of FIG. 2, FIG. 5 a schematic radial sectional view of another embodiment according to the invention of a corresponding electrically insulating substrate with additional layers, FIG. 6 a schematic radial sectional view of a portion of an embodiment according to the invention, FIG. 7 a schematic sectional representation along A-A in accordance with FIG. 6, FIG. 8 a schematic radial sectional representation through the inner area of a surgical instrument, FIG. 9 a schematic axial sectional representation along BB from FIG. 8, FIG. 10 a schematic portion of a longitudinal cut through a surgical instrument according to the invention, FIG. 11 a schematic three-dimensional representation of a portion of FIG. 10 in an alternative embodiment, FIG. 12 a schematic lateral view of a portion of the body from FIG. 11 in another embodiment and FIG. 13 a schematic lateral view of a portion of another embodiment according to the invention.

In the following figures, the same or similar elements or respectively corresponding parts have the same reference numbers so that a corresponding reintroduction is omitted.

FIG. 1 shows schematically a longitudinal cut through a system tube of a video endoscope according to the state of the art from DE 10 2006 015 176 B3.

FIG. 1 shows a rigid medical video endoscope 1 with a system tube 2 made of metal, which is closed on the distal end with a soldered in window 3, behind which a schematically shown objective 4 and a video camera 5 are arranged in the distal end area of the system tube 2, which is connected to the outside via the lines. In the simplified example in FIG. 1, these are two electrical lines 6.

The electrical lines 6 run through the proximal opening 7 of the system tube 2, the proximal opening being closed with a potting material 8. The electrical lines 6 are designed in this area as non-insulating feed-through conductors 9. According to the usual state of the art, glass, which is melted in liquid form into the system tube 2 and around the feed-through conductors 9, is provided for sufficient hermetic sealing of the interior of the system tube 2 as potting material 8. A simple design of the potting material 8 made of plastic can lead to insufficient gas permeability.

FIG. 2 shows schematically a part of a surgical instrument 1 according to the invention, for example a video endoscope, a laparoscope, an endoscope or a similar instrument in a first embodiment according to the invention, wherein the part is shown, which is represented for a hermetic sealing of a hermetic chamber 19 from an outer area 20.

In this exemplary embodiment, the system tube 2 is designed cylindrically. It can however also have other shapes. For the hermetic through connection or respectively for the hermetic electrical connection, a conductor path structure in the form of feed-through conductors 9, $9^I$ and other feed-through conductors, which are then shown in FIG. 3, are applied to the exterior of a cylindrical substrate 21, which preferably has a non-electrically conductive but thermally conductive material.

The application of the conductor path structure can occur by means of printing, CVD, magnetic sputtering, laser ablation and the like.

An insulating layer 14 is then applied and on the insulating layer a metal layer 15. Adjacent to the metal layer 15 is the wall 16, which leads to the system tube 2. The wall is hermetically soldered with the system tube 2 and the metal layer 15. A hermetical sealing of the hermetic chamber 19 is hereby enabled.

For the through contacting or respectively for the connection with the corresponding lines, flexible conductor plates 10, 11, 12, 13 are provided, which are electrically connected with a corresponding solder 18 also with the respective conductor path 9, $9^I$ and also the other conductor paths from FIG. 3. It can be seen that on the end surfaces of the substrate the conductor paths or respectively the feed-through conductors 9, $9^I$ and also the other feed-through conductors $9^{II}$-$9^{VIII}$, which are shown in FIG. 3, are exposed. The insulating layer 14 and the metal layer 15 are arranged completely around the substrate 21. The substrate can be a ceramic, which is named above.

For stabilization of the flexible conductor plates 10, 11 on the proximal end of the surgical instrument or respectively video endoscope 1, they can be potted for example with plastic. The soldering points 18 or respectively the flexible conductor plates 10, 11 can hereby be protected from tensile loading.

FIG. 3 shows schematically a cross-section through the feed-through device with the substrate 21 as per FIG. 2. The feed-through conductors 9-$9^{VIII}$ can be vapor-deposited and structured. Accordingly, the insulating layer 14 and the metal layer 15 can also be vapor-deposited. It can be seen that the substrate 21 is round in cross-section. The corresponding feed-through conductors 9-$9^{VIII}$ are arranged symmetrically around the substrate 21. The insulating layer 14 is arranged around them and around it the metal layer 15. The insulating layer 14 can be a silicon dioxide or a silicon nitride or another ceramic. The feed-through conductors 9-$9^{VIII}$ can be made of gold, copper or silver. The outer metal layer, which can also be called a solder layer, can for example be made of gold.

FIG. 4 shows another section representation of a portion of the embodiment as per FIG. 3, without the wall 16 for better illustration.

FIG. 2 through 4 show an embodiment without shielding. Whereas FIG. 5 shows a schematic sectional representation of an embodiment with shielding, it can be seen that an intermediate layer 22, which can be a metal layer and serves for shielding together with the solder and shielding layer 23, is first provided around the substrate 21. The conductor paths or respectively feed-through conductors 9-$9^{VIII}$ are arranged on an insulating layer 24. A second insulating layer 25 is arranged around the feed-through conductor 9-$9^{IV}$. The corresponding layer and the feed-through conductors can also be vapor-deposited accordingly. The insulating layers 24 and 25 can be made of silicon nitride, silicon dioxide or another ceramic.

FIG. 6 shows a schematic representation of a feed-through device according to the invention in a longitudinal, axial sectional representation. A rectangular flexible conductor plate 100 is provided as the substrate, which can also be made of a plastic.

FIG. 7 shows a schematic sectional representation along A-A of FIG. 6. Five feed-through conductors 9-$9^{IV}$ are applied around the flexible conductor plate 100, of which three are applied above the conductor plate 100 and two below the conductor plate 100. The feed-through conductors 9-$9^{IV}$ can also be an integral component of the conductor plate 100. Feed-through conductors can also be applied to the sides or a different number of feed-through conductors can be applied.

An insulating layer 14 is provided around the feed-through conductor and the flexible conductor plate 100. A metal layer 15 is provided around the insulating layer 14. In the sectional view, the insulating layer 14 and the metal layer 15 completely surround the substrate with the feed-through conductors 9-$9^{IV}$ here.

On the edges, i.e, indicated left and right in FIG. 6, two other insulating layers 26 and 27 are applied around the metal layer 25 or respectively on the metal layer 25. These layers are, as shown in FIG. 6, not applied in the middle area and are not applied to the end areas either, which is not shown in FIG. 6, in order to enable a corresponding connection of the feed-through conductors 9 through $9^{IV}$.

A connection with a corresponding first half shell 28 and the corresponding second half shell 29 to the system tube 2 (not shown) is represented in FIG. 9. A hermetic solder 32 is also represented there.

FIG. 8 shows a structure, which is inserted into a system tube 2 (not shown), provided around a hermetic sealing. A first half shell 28 and a second half shell 29, which are hermetically joined at the joints 30 and 31, are provided. The solder, which enables a connection with the system tube 2 (not shown) is then applied on the outer edge of the half shells 28 and 29. This also concerns a hermetic connection. The hermetic connection with the feed-through device comprising the flexible conductor plate 100, the feed-through lines not shown in FIG. 8 for better illustration, the insulating layer 14 and the metal layer 15, on which the solder 32 is applied, are also shown in FIG. 8. The insulating layer 26 is also shown schematically. It protrudes over the opening for the feed-through device resulting from the half shells 28, 29.

Through the embodiments according to FIGS. 6 through 9, a particularly simple feed-through of conductors is possible since a flexible conductor plate, which is connected in the hermetic chamber with corresponding electrical components, is led through directly. The corresponding layers are also applied, e.g. vapor-deposited, on the flexible conductor plate 100. A potential creep distance between the applied layers of the flexible conductor plate 100 can be extended by the applied insulating layer 26 and 27. An electrical plating-through can hereby take place directly and without further soldering points or plug connections. A hermetic soldering is nonetheless present. The dimensions that can be used in the feed-through device according to the invention are considerably smaller than for conventional solutions with hermetic plugs. Considerably thinner tubes can hereby be used.

FIG. 10 shows a schematic portion of a longitudinal cut through a surgical instrument according to the invention in another embodiment. A hermetically sealed area 19 and a non-hermetic chamber 20 are also provided here. For the connection of these two areas and for the feed-through of electrical lines, an insulating body 40 is provided, to which electrical lines in the form of electrically conductive layers are applied, for example printed. The insulating body 40 is connected with the tube 52 via a glass-potted connector 42. A hermetic connection is hereby created. The tube 52 can be the outer tube of the surgical instrument 1, but can also be connected with the outer tube of the surgical instrument, in particular hermetically. The conductor paths or respectively electrical connections $9\text{-}9^{VIII}$ can, as indicated for example in FIG. 10, be printed or vapor-deposited on the surface of the insulating body 40. These can hereby be metal layers that are arranged in the longitudinal extension of the insulating body.

FIG. 11 shows a schematic three-dimensional representation of another embodiment of the insulating body 40. Corresponding grooves 41 are made in the surface of the insulating body 40. Corresponding electrical connections each in the form of a feed-through conductor $39\text{-}39^{VIII}$ provided on the floor of the grooves 40. A fit groove 43 is provided for a clear assignment of the corresponding electrical connections with a connection plug. Alternatively, an eccentric blind hole can also be provided, which can be connected with a correspondingly fitting pin of a plug attachable to the insulating body 40.

FIG. 12 shows a section of a lateral view of the insulating body 40, in a further embodiment, wherein rectangular grooves are provided along the longitudinal axis of the insulating body 40. The grooves are labeled with reference number 41. Corresponding feed-through conductors 39 through $39^{IV}$ are provided in the grooves. Further feed-through conductors $9\text{-}9^V$ are arranged on another level, namely on the outer surface of the insulating body 40. In the case of a circumference of for example 31.4 mm, which corresponds to a diameter of 10 mm of the insulating body 40, more than 400 conductor paths with a width of 75 μm can hereby be accommodated. A second level of conductor paths is created through the use of small rectangular longitudinal grooves distributed over the circumference.

FIG. 13 shows another embodiment of the insulating body 40 in a schematic lateral view. V-shaped grooves are made longitudinally axially in the insulating body 40. The feed-through conductors 39 through $39^{VIII}$ are applied on the respective left flank of the respective groove 41'. It is provided that a feed-through conductor is arranged in each groove. The fit groove 43 is also provided here. Through this embodiment, in which corresponding V grooves are provided along the cylinder surface of the insulating body 40, for example of a ceramic pin, and a corresponding metallization of a flank of the V groove, it is possible, for example in the case of a height of the flank of 45 μm at a diameter of the insulating body of 10 mm, to provide approximately 300 conductor paths in a corresponding pin or respectively insulating body 40.

Moreover, it is shown in FIG. 13 that the groove 43 also has a conducting layer 44, by means of which a contacting can also be performed. For example, the mass can be conducted from the hermetically sealed area towards outside the hermetically sealed area or respectively vice versa.

All named characteristics, also those taken solely from the drawings as well as individual characteristics disclosed in combination with other characteristics, are considered important for the invention both alone and in combination. Embodiments according to the invention can be fulfilled by individual characteristics or a combination of several characteristics.

LIST OF REFERENCE NUMBERS

1 Video endoscope
2 System tube
3 Soldered in window
4 Objective
5 Video camera
6 Electrical line
7 Proximal opening
8 Potting material
9 Feed-through conductor
$9^I$ Feed-through conductor
$9^{II}, 9^{III}, 9^{IV}, 9^V, 9^{VI}$, Feed-through conductor
$9^{VI}, 9^{VII}, 9^{VIII}$ Feed-through conductor
10 Flexible conductor plate
11 Flexible conductor plate
12 Flexible conductor plate
13 Flexible conductor plate
14 Insulating layer
15 Metal layer
16 Wall
17 Hermetic solder
18 Solder
19 Hermetic chamber
20 Non hermetic chamber
21 Substrate
22 Intermediate layer
23 Solder and shielding layer
24 Insulating layer
25 Insulating layer
26 Insulating layer
27 Insulating layer
28 First half shell
29 Second half shell
30 Joint
31 Joint
32 Hermetic groove
39, $39^I, 39^{II}, 39^{III}, 39^{IV},$
$39^V, 39^{VI}, 39^{VII}, 39^{VIII}$ Feed-through conductor
40 Insulating body
41, 41' Groove
42 Glass-potted connector
43 Fit groove
44 Conducting layer
52 Tube
100 Flexible conductor plate

The invention claimed is:
1. A surgical instrument comprising:
a wall that extends radially inward from a tube;

an electrically insulating substrate arranged within the tube;

an electrical connection, wherein at least a portion of the electrical connection is applied on an exterior surface of the electrically insulating substrate;

an insulating layer applied on an exterior surface of the portion of the electrical connection, wherein the insulating layer extends radially outward from the exterior surface of the portion of the electrical connection towards the wall, and wherein the insulating layer is comprised of a different material than the portion of the electrical connection applied on the exterior surface of the electrically insulating substrate; and a hermetic connection layer applied on the insulating layer, wherein the hermetic connection layer extends radially outward towards the wall and is hermetically connected to the wall to hermetically separate a chamber within the tube from an outer area, wherein the wall comprises:
   a first shell; and
   a second shell joined together hermetically with the first shell to define an opening in which the electrically insulating substrate, the portion of the electrical connection, the insulating layer, and the hermetic connection layer are arranged,
   wherein the wall extends radially inward between the tube and the opening by a radial distance, and the wall extends along a longitudinal axis of the tube by an axial distance that is less than the radial distance, and
   wherein an outer edge of the first shell and an outer edge of the second shell are connected to a portion of an inner surface of the tube between a first end of the tube and a second end of the tube along the longitudinal axis of the tube.

2. The surgical instrument according to claim 1, wherein the hermetic connection layer is a soldering.

3. The surgical instrument according to claim 1, wherein the electrically insulating substrate has a thermal conductivity of more than 1 W/mK.

4. The surgical instrument according to claim 3, wherein the thermal conductivity is greater than 200 W/mK.

5. The surgical instrument according to claim 1, further comprising:
   a flexible conductor plate configured to electrically contact the electrical connection.

6. The surgical instrument according to claim 1, wherein the electrical connection is completely arranged around the exterior surface of the electrically insulating substrate.

7. The surgical instrument according to claim 6, further comprising a plurality of the electrical connection, wherein the plurality of the electrical connection are provided symmetrically around the electrically insulating substrate.

8. The surgical instrument according to claim 1, wherein the at least a portion of the electrical connection is applied on the exterior surface of the electrically insulating substrate by metallization.

9. The surgical instrument according to claim 1,
   wherein the electrically insulating substrate defines a groove extending longitudinally axially, and
   wherein the at least a portion of the electrical connection is arranged in the groove.

10. The surgical instrument according to claim 9, wherein the groove has a rectangular cross-section.

11. The surgical instrument according to claim 9, wherein a portion of the electrical connection is provided outside the groove.

12. The surgical instrument according to claim 9, wherein the groove has a V-shaped cross-section.

13. The surgical instrument according to claim 10,
   wherein a portion of the exterior surface of the electrically insulating substrate forms a flank of the groove having the V-shaped cross-section, and
   wherein the electrical connection is applied to the flank of the groove having the V-shaped cross-section.

14. The surgical instrument according to claim 1, further comprising the tube, wherein the tube is an endoscope.

15. The surgical instrument according to claim 14, wherein the endoscope is a laparoscope.

* * * * *